US005547873A

United States Patent [19]

Magneson et al.

[11] Patent Number: 5,547,873

[45] Date of Patent: Aug. 20, 1996

[54] COMPOSITIONS FOR STABILIZING PROTEINS FOR LONG TERM DRY STORAGE AND METHODS OF MAKING AND USING THE COMPOSITIONS

[75] Inventors: Gerald R. Magneson, Needham, Mass.; David L. Reichenbach, Pembroke Pines, Fla.

[73] Assignee: Genzyme Corporation, Cambridge, Mass.

[21] Appl. No.: 198,430

[22] Filed: Feb. 22, 1994

[51] Int. Cl.$^6$ ................................. G01N 31/00
[52] U.S. Cl. .................. 436/18; 436/8; 436/15; 436/16
[58] Field of Search ................. 436/518, 8, 13, 436/15, 16, 17, 18, 66, 71; 435/188

[56] References Cited

U.S. PATENT DOCUMENTS

| | | | |
|---|---|---|---|
| 4,127,502 | 11/1978 | Li Mutti et al. | 436/16 |
| 4,158,544 | 6/1979 | Louderback | 436/16 |
| 4,684,615 | 8/1987 | Hoskins | 436/16 |
| 4,701,417 | 10/1987 | Portenhauser et al. | 436/13 |
| 4,762,857 | 8/1988 | Bollin, Jr. et al. | 514/777 |
| 4,883,762 | 11/1989 | Hoskins | 436/18 |
| 5,155,025 | 10/1992 | Allen et al. | 435/11 |
| 5,348,852 | 9/1994 | Bonderman | 435/4 |

OTHER PUBLICATIONS

Warnick, G. et al. (1978) "Comparison of Current Methods for High–Density Lipoprotein Cholesterol Quantitation" Clin. Chem., 25(4):596–604.

Rifai, N. et al. (1992) "Measurement of Low–Density Cholesterol in Serum: a Status Report" Clin. Chem. 38(1):150–160.

Scott et al. Concise Encyclopedia of Biochemistry ©1988 Pub: Walter de Gruyter, NY pp. 342–345.

Medical World News vol. 34 Issue: n3 p. 70(1); Mar. 1993 "Lab Kit tests directly for LDL Cholesterol".

The Sigma Catalogue, 1992 p. 835.

Scopes, Robert K., "Protein Purification Principles and Practice" Second edition; 1987 by Springer–Verlag, New York pp. 251–252.

Primary Examiner—Marian C. Knode
Assistant Examiner—Patricia A. Duffy
Attorney, Agent, or Firm—William G. Gosz, Esq.

[57] ABSTRACT

The invention relates to a composition for stabilizing proteins for long term dry storage and superior recovery of their native protein structure for extended reconstituted stability at 2°–8° C. The composition comprises: 1) a defibrinated sodium-free blood plasma, 2) a glass-forming sugar, 3) a serum albumin and/or a gelatin, and 4) a potassium salt. In another aspect, the present invention relates to a method for stabilizing a protein for long term dry storage using the above mentioned composition.

11 Claims, No Drawings

COMPOSITIONS FOR STABILIZING PROTEINS FOR LONG TERM DRY STORAGE AND METHODS OF MAKING AND USING THE COMPOSITIONS

BACKGROUND OF THE INVENTION current serum-based calibrator and quality control products used for measuring lipid and lipoprotein levels have been plagued with difficulties in stabilizing these materials for long term dry storage, because of the tendency for β-lipoproteins such as LDL and VLDL to denature and/or aggregate due to their large molecular size and hydrophobic nature. In some instances, clinical chemistry laboratories have resorted to preparing human lipid quality controls by pooling patient serum containing different lipoprotein concentrations for short term use and storage at 2°–8° C. Due to the time-consuming nature and hazards associated with handling blood serum from multiple human samples to prepare serum pools, commercially available lyophilized quality control materials gained wide acceptance.

Unfortunately, many of these human blood plasma-based lyophilized control materials suffer from matrix effects caused by denaturation and/or aggregation of their protein components, especially endogenous LDL and VLDL, which can cause interferences in clinical chemistry measurements due to matrix turbidity. In order to circumvent such problems, many lipid quality control materials are formulated using either an animal serum base (i.e., endogenous TC is predominantly HDL) supplemented with HDL to elevate TC, or human delipidated plasma supplemented with HDL. Hence, there is a need for quality control products that stabilize human cardiovascular marker proteins, especially LDL (clinical studies indicate that there is a strong correlation between increased serum LDL and the incidence of coronary heart disease), to enable its direct measurement and/or detection with reagents/devices employing a new generation of more sensitive and specific immunoseparation/immunochemical assay technologies (Rifai, N. et al., Clin. Chem. 38:150–160, 1992).

SUMMARY OF THE INVENTION

This invention pertains to a composition in part containing defibrinated, sodium-free blood plasma that is diafiltered to exchange endogenous sodium with a potassium salt, diluted with serum albumin, and supplemented with a glass-forming sugar to stabilize protein structural integrity for long term dry stability (i.e., >5 months shelf life at about 2°–8° C., for a protein with a residual moisture <5% weight per volume (w/v)) and subsequent extended reconstituted stability (i.e., >10 days shelf life at about 2°–8° C. for a the reconstituted protein). The composition comprises: 1) a defibrinated sodium-free blood plasma, 2) a glass-forming sugar, 3) a serum albumin and/or a gelatin, and 4) a potassium salt. In another aspect, the present invention relates to a method for stabilizing a protein for dry storage using the above mentioned composition.

The invention further relates to a method for producing a stabilizing buffer for the dry storage of a protein. The method comprises: 1) defibrinating blood plasma, 2) diafiltering the product of step 1) with an aqueous solution containing a potassium salt, 3) diluting the product of step 2) with an aqueous solution containing a protein compromising: 1) a glass-forming sugar, 2) a serum albumin and/or gelatin, and 3) a potassium salt, and 4) removing essentially all of the aqueous component of the product of step 3). The invention also relates to reconstituting the product by adding water, or an aqueous buffer containing a salt and/or a preservative.

DETAILED DESCRIPTION OF THE INVENTION

This invention relates to a blood plasma or plasma-derived composition containing lipoproteins and other cardiovascular markers in a quality control material, which has been stabilized for long term dry storage and to recover essentially all of their native protein structural determinants, or immunological epitopes upon reconstitution with water. In particular, this invention pertains to a freeze dry lyophilized human serum-based calibrator\control material that stabilizes its endogenous and exogenous lipoprotein and cardiovascular marker protein(s) structural integrity for long term shelf-life and extended reconstitution stability for use either in diagnostic device(s) for immunoseparation of lipoproteins or as a standard clinical chemistry control to assist in the measurement of clinically significant cardiovascular analytes such as: total cholesterol (i.e., TC); very-high-density lipoprotein cholesterol (i.e., VHDL); intermediate-density lipoprotein cholesterol (i.e., IDL); low-density lipoprotein cholesterol (i.e., LDL); lipoprotein(a) cholesterol (i.e., Lp(a)); high-density lipoprotein cholesterol (i.e., HDL); apolipoprotein isoforms such as A, apo Lp(a), B, C, D, E, F, G, and H; isoenzymes such as creatine kinase, lactate dehydrogenase, alkaline phosphatase, and carbonic anhydrase; cytoskeletal protein isoforms such as troponin and myosin light chain; and cardiovascular marker/protein(s) such as myoglobin and triglycerides (i.e., TAG).

A principle component of the composition of the present invention is blood plasma which includes fresh frozen blood plasma, recovered or "blood-bank" blood plasma, source or plasmaphoresis blood plasma, off-clot true blood serum, and other mammalian-derived plasmas or serums.

Fresh frozen blood plasma is a single donation of whole blood that is collected into a plastic bag containing an anti-coagulant solution, CPDA-1, comprising citrate, phosphate, dextrose, and adenosine. After collection, plasma is separated from the blood cells and frozen within twelve hours at or below −18° C.

Recovered or "blood-bank" blood plasma is a single donation of whole blood that is collected into a plastic bag containing an anti-coagulant solution, such as ACD, comprising adenosine, citrate, and dextrose, such as EDTA, and such as heparin. After collection, plasma is separated from the blood cells and stored at ambient temperature or at 2°–8° C. or at or below −18° C.

Source or plasmaphoresis blood plasma is a single, or double donation of blood plasma that is collected free from blood cells into a plastic bag, or a glass bottle containing sodium citrate, an anti-coagulant. After collection, plasma is stored at or below −18° C.

Off-clot true blood serum is a single donation of whole blood that is collected into a plastic bag, or a glass bottle in the absence of an anti-coagulant solution, allowed to coagulate via the activation of the native coagulation cascade system, and separated from the blood cell clot. After collection, off-clot true blood serum is stored at 2°–8° C. or at or below −18° C.

Mammalian-derived plasmas or serums include blood plasma or serum collected from single, or multiple donors from mammalial sources, such as bovine, equine, goat, murine, ovine, or porcine serum, in plastic bags, or glass bottles and separated from blood cells via the means described above. After collection, mammalian-derived plasmas or serums are stored at 2°–8° C. or at or below −18° C.

For purposes of the present invention, the blood plasma component is defibrinated. Any defibrination procedure known to those of skill in the art is suitable. An example of a defibrination method includes: supplementing plasma with a mammalian-derived thrombin and a calcium salt, mixing the solution at room temperature to convert fibrinogen to fibrin, and filtering out the fibrin clot.

In one of the key steps in the current invention, the defibrinated blood plasma is diafiltered or dialyzed against a solution containing a potassium salt, the resulting blood plasma product being sodium-free (i.e., a diafiltered and diluted sodium concentration of <10 mM). Any diafiltering, dialyzing, chromatographic, and/or other method known to those of skill in the art, which allows the exchange of potassium for the sodium salt in blood plasma, is suitable in the present invention, provided the structural integrity of the subject protein is maintained. Preferrably, the defibrinated, sodium-free blood plasma is used at concentrations of total protein, which is about equal to that present in native blood serum. Although it should be noted that blood plasma protein concentrations below 4 g/dL may be sufficient for purposes of the current invention.

The composition of the present invention, in addition, contains a glass-forming sugar such as a reducing monosaccharide or disaccharide sugar, or a nonreducing monosaccharide or disaccharide sugar, or a sugar alcohol. The term, "glass-forming sugar", is intended to include the sugars listed above, or a mixture thereof. In the present invention, the group of reducing and non-reducing monosaccharide sugars include arabinose, xylose, glucose, fructose, galactose, and mannose at a concentration of between about 10 and 30% (w\v). The group of reducing and non-reducing disaccharides include lactose, maltose, cellobiose, raffinose, sucrose, and trehalose at a concentration of about 10 and 30% (w/v). In addition, the group of sugar alcohols include mannitol, xylitol, and sorbitol at a concentration of between about 10 and 30% (w\v).

The composition of the present invention further contains serum albumin. Suitable serum albumin include those that are mammalian-derived.

In addition, the composition of the present invention contains a gelatin. Suitable gelatins include those that are mammalian-derived, fish-derived, and/or vegetable-derived.

As explained above, the endogenous sodium salt present in blood plasma is exchanged for a potassium salt. Suitable potassium salts include potassium chloride, potassium sulfate, potassium phosphate, potassium nitrate, and/or other soluble potassium salts.

It should be noted that reconstituted liquid storage of a plasma-based control material at 2°–8° C. typically requires the inclusion of preservatives and/or sterile procedures to prevent contamination by microbial growth. Typical preservatives include methyloxazolidine derivatives, gentamycin sulfate, and methyl-isothiazolin-one derivitives. The preferred embodiment in the present invention is 0.1% (w/v) gentamycin sulfate.

For cosmetic purposes, bilirubin may be added to blood plasma to give the appearance of normal, or diseased plasma, where the preferred embodiment in the present invention is to impart a normal appearance by adding sufficient total bilirubin to give a final concentration of about 0.5 to 0.8 mg/mL.

EXAMPLES

The present invention can be clearly demonstrated by using representative examples that show the discrepancy between the functionality of a human plasma-based, lyophilized quality control material that is stabilized for optical clarity and one that contains lipoproteins and cardiovascular marker proteins stabilized to recover essentially all of their structural determinants, or immunological epitopes upon reconstitution. Optical density (O.D.) values relate to Beer's Law (i.e., O.D.= $I_o/I$), wherein $I_o$ is the intensity of the incident light and I is the intensity of the transmitted light. For all O.D. examples used wherein, the wavelength of the incident light was 710 nm, which was read at a pathlength of 1 cm using either a Gilford Stasar III, or a Beckman spectrophotometer. For all examples of the recovery of LDL cholesterol used wherein, the recovered LDL value was determined by dividing the reconstituted direct LDL value (i.e., the total cholesterol measured from the filtrate of a sample treated using the Direct LDL Cholesterol Immunoseparation Reagent Kit (Genzyme Diagnostics, Cambridge, Mass.) to selectively remove HDL and VLDL using antibody-coated latex beads) by the pre-lyophilization LDL concentration, which was indirectly determined by using Friedewald's Equation (i.e., TC=HDL+LDL+TAG/5, or LDL=TC−HDL−TAG/5).

Examples 1–9

The plasma bases used in Table 1 were prepared using individual donor units of fresh frozen human blood plasma and recovered human blood plasma. Each type of plasma was processed at different times. Units were first thawed at ambient temperature, pooled, and defibrinated as follows: added 0.34 g of $CaCl_2$ per mL of deionized water per liter of human plasma; immediately after addition of $CaCl_2$, added an aqueous solution containing 3.5 mg bovine thrombin (i.e., with about 80–100 NIH Units) per liter of plasma; mixed the treated plasma at ambient temperature for $\geq 30$ minutes, or until fibrinogen (i.e., Factor I) is not detected using a Factor I assay kit (Baxter Diagnostics Inc., McGaw Park, Ill.). Then, the defibrinated human blood plasma is stored frozen at −18° C. for at least 25 days prior to any further processing.

To investigate the possible stabilizing effect that freeze/thaw cycling may have on this product, an aliquot of defibrinated human plasma was subjected to the following freeze/thaw process four times: frozen plasma was thawed completely at ambient temperature and then, refrozen at −18° C., and stored for at least 5 days (before repeating this cycle).

Defibrinated plasma was diafiltered using a Millipore pellicon BSA cassette device (Millipore Corporation, Bedford, Mass.) with a flat sheet membrane (molecular weight (MW) exclusion size of 30,000 Daltons). The plasma was diafiltered across this membrane using a peristaltic pump, generating a transmembrane pressure of up to 20 p.s.i. for a molecular flux rate of about 150 mL plasma per minute. About 3–4 volumes of an aqueous solution containing either 9.0 g/L NaCl, or 7.8 g/L KCl were employed for diafiltration of a volume of the different plasma bases to either obtain a final NaCl concentration of about 100 mM, or to reduce the endogenous sodium level to less than 20 mM, while raising the potassium level to about 100 mM, respectively. After the salt exchange was achieved, the system was used to concentrate the plasma base by ultrafiltration to attain a total protein concentration of between 8 and 14 mg/dL. This material was stored frozen at −18° C. prior to further processing.

To complete the formulation of these control pilots, the diafiltered and ultrafiltered defibrinated blood plasmas were thawed at ambient temperature. To certain pilots, sucrose or trehalose was added as a solid to give a final concentration of 20% (w/v). Next, to all pilots was added solid gentamycin sulfate to give a concentraton of 0.1 mg/mL. Then, bilirubin was added to each pilot to a concentration of between 0.5 to 0.8 mg/dL. Next, the pH of the plasma base was adjusted to 7.4±0.2 using 2N KOH. Finally, these pilots were filtered through a series of filters terminating with a 0.22μ final sterile filter.

Aliquots, 2.3 mL, of each pilot were filled into glass vials (10 cc Wheaton, Type I) and freeze dry lyophilized in a FTS Tray Dryer (FTS Systems, Inc., Stone Ridge, N.Y.). After the vials were stoppered under a nitrogen gas environment, these pilots were stored at 2°–8° C. until tested.

The pre-lyophilization pilot values for TC, HDL, and TAG were determined by National Health Laboratories (Miami, Fla.) using Olympus reagents on an Olympus AU5000 Chemistry Analyzer (Olympus Corporation, Lake Success, N.Y.). LDL cholesterol was indirectly determined using the Friedewald's Equation as described above. The direct LDL concentration in reconstituted pilot vials was determined using the Direct LDL Immunoseparation Reagent kit (Genzyme), assaying filtrate TC on an Abbott VP Analyzer (Abbott Diagnostics, Abbott Park, Ill.) using DCL Cholesterol reagent (Diagnostics Chemicals Limited, Charlottetown, P.E.I., Canada).

TABLE 1

| Treatment/ Plasma Base | Freeze/ Thaw Cycles | Sugar | Diaf. Salt | O.D. | % Recovery of LDL |
| --- | --- | --- | --- | --- | --- |
| 1-Rec. Plasma, unlyophilized | none | none | Na | 0.10 | 100 |
| 2-Rec. Plasma, lyophilized | none | none | Na | 0.96 | N/A |
| 3-Rec. Plasma, lyophilized | four | none | Na | 0.73 | N/A |
| 4-Rec. Plasma, lyophilized | four | trehalose | Na | 0.33 | N/A |
| 5-Rec. Plasma, lyophilized | four | sucrose | Na | 0.15 | 30 |
| 6-Rec. Plasma, lyophilized | four | sucrose | K | 0.16 | 27 |
| 7-F.F. Plasma, lyophilized | four | sucrose | Na | 0.24 | 74 |
| 8-F.F. Plasma, lyophilized | four | sucrose | K | 0.12 | 98 |
| 9-F.F. Plasma, lyophilized | none | sucrose | K | 0.09 | 99 |

Table 1 demonstrates that in the absence of a glass-forming sugar, treatment of diafiltered recovered plasma by freeze/thaw cycling only slightly reduces the turbidity of the reconstituted sample (see Examples 1–3). However, the addition of 20% (w/v) trehalose or sucrose stabilizes lyophilized recovered plasma to give an optically clear reconstituted control material, which fails to recover more than 30% of its endogenous LDL (see Examples 4–6).

It should be noted that the identity of the salt present in Examples 5 and 6 has no significant effect on the recovery of LDL, because the endogenous LDL is, undoubtedly, already damaged and/or aggregated in this recovered plasma base, such that the beneficial effect of the potassium salt can not be observed. In contrast, the pilot formulation for Example 7 shows that defibrinated fresh frozen plasma diafiltered with NaCl has a recovery of about three quarters of its endogenous LDL and also exhibits excellent optical clarity (see Table 1). However, when sodium is exchanged for potassium, essentially all of the endogenous LDL in the fresh frozen human plasma base is recovered, because the native lipoprotein structure is maintained during lyophilization (in the presence or absence of freeze/thaw cycling—see Examples 8 and 9).

Example 10–13

In order to validate the feasibility of a bilevel cardiovascular marker quality control material using endogenous and/or exogenous lipoprotein fractions to vary the final HDL and LDL levels, two different formats were constructed using the defibrinated and sodium-free human blood plasma formulation described in Example 9, with the following exceptions: 1) in the LDL concentration format, endogenous LDL and HDL concentrations were increased by the concentration of the plasma base via ultrafiltration, and 2) in the LDL supplementation format, LDL and HDL concentrations were adjusted by dilution of the plasma base to lower the endogenous HDL level and increasing the LDL level by supplemention with a human LDL concentrate (Creative Laboratory Products Inc., Indianapolis, Ind.). In these studies, each format was formulated to have one pilot recover a LDL concentration that is lower than the clinically significant normal LDL range as defined by the National Cholesterol Education Program (NCEP) guidelines (i.e., a Desirable level of <130 mg/dL LDL) and to have the other pilot recover a LDL level greater than that of the clinically significant abnormal LDL range as defined by the NCEP guidelines (i.e., a Risk level of >160 mg/dL LDL).

For the LDL concentration format, a defibrinated and sodium-free fresh frozen human blood plasma composition for the Desirable level pilot (Example 10) was prepared as described above in Example 9, but the Risk Level plasma base was ultrafiltered for a greater time interval to concentrate the plasma proteins to increase its endogenous LDL value (see Example 11 in Table 2).

For the LDL supplementation format, a defibrinated and sodium-free fresh frozen human blood plasma composition for the Desirable level pilot (Example 13) was prepared as described above in Example 9, but the method for preparing the Risk Level plasma base was changed in the following manner: 1) its base material was diluted with an aqueous solution containing 7 g/dL bovine serum albumin and 7.8 g/L KCl to decrease the endogenous HDL level to about 15–25 mg/dL just prior to the addition of the sucrose component; and 2) the diluted Risk level pilot was supplemented with sufficient LDL concentrate (Creative Laboratory Products Inc.) to give a final concentration of about 170 mg/dL just after the pH was adjusted.

Aliquots, 1.0 mL, of each pilot were filled into glass vials (10 cc Wheaton, Type I) and freeze dry lyophilized in a FTS Tray Dryer (FTS Systems, Inc., Stone Ridge, N.Y.). After the vials were stoppered under a nitrogen gas environment, these pilots were stored at 2°–8° C. until tested.

In these examples, pre-lyophilization pilot values for TC, HDL, TAG, and indirect LDL were determined as described above. In reconstituted samples, the direct LDL concentration was determined using the Direct LDL Cholesterol Immunoseparation Reagent kit (Genzyme), assaying filtrate TC on a Roche COBAS FARA II Chemistry Analyzer using Roche Cholesterol reagent (Roche Diagnostics, Nutley, N.J.). Furthermore, TC and HDL also were measured on the Roche COBAS FARA II Chemistry Analyzer. HDL values were obtained using the dextran sulfate-magnesium chloride method as described by Warnick and co-workers (Warnick, G. R. et al., Clin. Chem. 25:596–604, 1979).

TABLE 2

| Treatment | O.D. | TC | HDL | Direct LDL | % Rec. LDL |
|---|---|---|---|---|---|
| 10-Desirable Lot, LDL Concentrated | 0.05 | 161 | 51 | 106 | 106 |
| 11-Risk Lot, LDL Concentrated | 0.20 | 233 | 69 | 146 | 99 |
| 12-Desirable Lot, LDL Supplemented | 0.04 | 157 | 46 | 100 | 102 |
| 13-Risk Lot, LDL Supplemented | 0.05 | 224 | 33 | 170 | 101 |

Table 2 shows that both formulation formats for a bilevel control appear to be viable choices to stabilize cardiovascular marker proteins, such as LDL. However, it is apparent that it would be more difficult to prepare the Risk level control by concentrating the plasma base to increase LDL concentration rather than using the LDL supplementation format with exogenous LDL (see Examples 11 and 13 in Table 2). Furthermore, the LDL supplementation format also facilitates the simulation of a true Risk patient lipoprotein profile, i.e., sample with an elevated LDL and an abnormally low HDL (see Examples 12 and 13). Hence, in the present invention, the LDL supplementation format is the preferred formulation, because it is more flexible in allowing for lipoprotein adjustments, and it is able to achieve desired product stabilization characteristics.

Examples 14–15

The reconstituted stability of a clinically significant cardiovascular marker protein, human CK-MB, was investigated to determine whether or not it exhibited extended liquid stability for compositions stored at 2°–8° C.

A defibrinated and sodium-free fresh frozen human blood plasma was prepared as described above in Example 9, with the following exceptions: 1) after the pH was adjusted, the base material for pilot A was supplemented with sufficient human CK-MB Antigen, Calibrator Grade (BioProcessing, Inc., Scarborough, Me.) to give a final CK-MB mass value of about 190 ng/mL; and 2) after the defribrinated and sodium-free fresh frozen human blood plasma was supplemented with sucrose and KCl, the pilot B formulation was supplemented with 1/100th volume of a HEPES buffer concentrate, pH 7.1±0.1, to give a final buffer concentration of 100 mM; and, 3) after the pH was adjusted to 7.4±0.2, the pilot B formulation was supplemented with sufficient human CK-MB Antigen, Calibrator Grade (BioProcessing, Inc.) to give a final CK-MB mass value of about 190 ng/mL.

Aliquots, 1.0 mL, of both pilot were filled into glass vials (10 cc Wheaton, Type I) and freeze dry lyophilized in a FTS Tray Dryer (FTS Systems, Inc., Stone Ridge, N.Y.). After the vials were stoppered under a nitrogen gas environment, these pilots were stored at 2°–8° C. until tested.

A single vial of each lyophilized control pilot was reconstituted with 1.0 mL of deionized water, mixed gentlely by swirling, and stored at 2°–8° C. until tested. Aliquots of each pilot were removed from vials on different days and restoppered for storage at 2°–8° C. The pre-lyophilization and reconstituted values for human CK-MB were determined by using Abbott $IM_x$ Human CK-MB reagents on an Abbott IMx Immunochemistry analyzer (Abbott Diagnostics, Abbott Park, Ill.). Percentage recovery vales were calculated by dividing the reconstituted CK-MB mass value by the pre-lyophilization value for each pilot on day zero.

TABLE 3

| Days Stored at 2–8° C. | 14-Pilot A % Recovery of CK-MB | 15-Pilot A % Recovery of CK-MB |
|---|---|---|
| 0 | 100 | 100 |
| 7 | 99 | 96 |
| 14 | 107 | 110 |
| 21 | 103 | 98 |

Table 3 demonstrates the excellent recovery of human CK-MB in reconstituted plasma-based control compositions of the current invention. Both pilot formulations stabilized human CK-MB mass for at least 21 days in vials repeated sampled and stored at 2°–8° C., which is superior to the liquid shelf life of most commercially available CK isoenzyme control materials, between 5 and 10 days (see Examples 14 and 15 in Table 3). Since the presence of HEPES buffer in the pilot B formulation appeared to decrease the observed concentration as measured by using the Abbott IMx immunochemistry analyzer (Abbott Diagnostics), the preferred current diafiltered and sodium-free blood plasma composition for stabilizing isoenzymes does not contain a pH buffer.

Equivalents

Those skilled in the art will recognize, or be able to ascertain, using no more than routine experimentation many equivalents to the specific embodiments of the invention described herein. Such equivalents are intended to be encompassed by the following claims:

The invention claimed is:

1. A composition for stabilizing a protein for long term dry storage, comprising:
   a. a defibrinated blood plasma with a sodium salt concentration of less than about 20 mM;
   b. a sugar selected from the group consisting of a reducing monosaccharide, a reducing disaccharide, non-reducing monosaccharide, a non-reducing disaccharide, and a sugar alcohol;
   c. a serum albumin or a gelatin or a mixture thereof; and
   d. a potassium salt wherein the concentration of the potassium salt is in the range of about 50 mM to 100 mM.

2. The composition of claim 1, wherein the blood plasma is from a mammal.

3. The composition of claim 1, wherein the serum albumin is from a mammal.

4. The composition of claim 1, wherein the gelatin is selected from the group consisting of gelatin from a mammal, and gelatin from a fish.

5. The composition of claim 1, wherein the potassium salt is potassium chloride.

6. A method for stabilizing a protein for long term dry storage, comprising:
   (a) adding an aqueous composition, comprising:
      i. a defibrinated and diafiltered human blood plasma with a sodium salt concentration of less than about 20 mM and a potassium salt concentration in the range of about 50 mM to 100 mM;
      ii. a sugar selected from the group consisting of a reducing monosaccharide, a reducing disaccharide, non-reducing monosaccharide, a non-reducing disaccharide, and a sugar alcohol; and iii. a serum albumin or gelatin or a mixture thereof; to a protein in a vessel; and (b) removing the water content of the product in step (a).

7. The method of claim 6, wherein the blood plasma is from a mammal.

8. The method of claim 6, wherein the gelatin is selected from the group consisting of gelatin from a mammal, and gelatin from a fish.

9. The method of claim 6, wherein the potassium salt is potassium chloride.

10. A method for producing a stabilizing buffer for the long term dry storage of a protein, comprising:

a. defibrinating blood plasma;

b. diafiltering the product of step a) with an aqueous solution containing a potassium salt to increase the potassium salt concentration to a range of about 50 mM to 100 mM while reducing the blood plasma sodium salt concentration to less than about 20 mM; and c. diluting the product of step b) with an aqueous solution, comprising:
  i. a serum albumin; or
  ii. a gelatin; or
  iii. a mixture thereof; and
  iv. a potassium salt in a concentration sufficient to maintain the potassium salt concentration in the range of about 50 mM to 100 mM; and d. adding a sugar selected from the group consisting of a reducing monosaccharide, a reducing disaccharide, non-reducing monosaccharide, a non-reducing disaccharide, and a sugar alcohol to the product of step c).

11. A method for stabilizing a protein for long term dry storage, comprising:

a. defibrinating blood plasma;

b. diafiltering the product of step a) with an aqueous solution containing a potassium salt to increase the potassium salt concentration to a range of about 50 mM to 100 mM while reducing the blood plasma sodium salt concentration to less than about 20 mM; and c. diluting the product of step b) with an aqueous solution, comprising:
  i. a serum albumin; or
  ii. a gelatin; or
  iii. a mixture thereof; and
  iv. a potassium salt in a concentration sufficient to maintain potassium salt concentration in the range of 50 mM to 100 mM; and d. adding a sugar selected from the group consisting of a reducing monosaccharide, a reducing disaccharide, non-reducing monosaccharide, a non-reducing disaccharide, and a sugar alcohol to the product of step c);

e. adding the protein to the product of step d);

f. removing the water content of the product of step e); and g. storing the product of step f).

* * * * *